US00PP07792P

United States Patent [19]

Drewlow

[11] Patent Number: Plant 7,792

[45] Date of Patent: Feb. 18, 1992

[54] KALANCHOE PLANT NAMED SPLENDOR

[75] Inventor: Lyndon W. Drewlow, Ashtabula, Ohio

[73] Assignee: Mikkelsens, Inc., Ashtabula, Ohio

[21] Appl. No.: 607,374

[22] Filed: Oct. 31, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A new and distinct cultivar of Kalanchoe plant named Splendor, characterized by its relatively large deep orange-red flowers, early flowering, large dark green leaves which are curled with crenate margins, excellent basal and lateral branching, excellent flower keeping quality, semi-mounded to semi-upright habit, and by its upright flowers above the foliage.

1 Drawing Sheet

The present invention relates to a new and distinctive cultivar of Kalanchoe plant, botanically known as Kalanchoe, and known by the cultivar name Splendor. Splendor was developed by me through controlled breeding by crossing Tropicana (seed parent) with Mikkelsen Seedling No. 84-2636-3 (pollen parent). Tropicana is disclosed in U.S. Plant Pat. No. 5,961.

Asexual reproduction by stem cuttings has shown that the unique features of Splendor are stabilized and are reproduced tru to type in successive propagations.

The following characteristics distinguish Splendor from both its parent varieties and other cultivated Kalanchoes of this type known and used in the floriculture industry, including the female or seed parent Tropicana. Color references are to The Legal Horticultural Society (R.H.S.) Colour Chart.

1. Splendor has a deeper orange-red (34A) flower color than Tropicana whose flowers are 33A in color.

2. Flowering time for Splendor is 3 to 5 days earlier than Tropicana under summer conditions and 7 to 10 days earlier under winter conditions from the start of short day treatment.

3. Average flower diameter of Splendor is 16 mm, while Tropicana has a 14 mm flower diameter.

4. Both Tropicana and Splendor have cuspidate petals. However, Splendor has a more cuspidate apex giving a pointed look, while Tropicana is only slightly cuspidate, thus giving a rounded appearance.

5. Average height of Splendor is 20 to 22 cm while Tropicana is 25 to 27 cm tall when grown under similar growing conditions.

6. Leaf color is similar for both Tropicana and Splendor. However, Splendor has a larger leaf, measuring 10 to 11 cm long and 9 to 9.5 cm wide, compared to Tropicana whose leaves are only 8 to 9 cm long and 5.5 to 6 cm wide.

7. Splendor has better basal and lateral branching. Under good growing conditions every node will usually produce a branch while Tropicana will only rarely produce a branch from each node.

8. Splendor has a curled leaf with crenate margins with some deep cut lobes, while Tropicana has a flat, crenate margin with no deep lobes.

9. Keeping quality of individual flowers of Splendor is 4 to 7 days longer than Tropicana flowers. The length of time plant remains in bloom after start of short day treatment is one week or longer for Splendor when compared to Tropicana.

10. Due to shorter internodes, peduncles and pedicels, and greater number of flowers in the cymes, there is a greater mass of flower color in Splendor than Tropicana. Overall appearance is semi-mounded to semi-upright on Splendor while Tropicana is very upright in growth habit.

The accompanying colored photograph illustrates in front perspective view the overall appearance of Splendor, showing the colors as true as it is reasonably possible to obtain in a colored reproduction of this type. The photograph was taken on Mar. 23, 1990 under natural light on an overcast day, and under double poly greenhouse covering at Ashtabula, Ohio.

The following is a detailed description of my new cultivar, based on plants produced in greenhouses in Ashtabula, Ohio during the late spring to summer season of the year. Plants were grown in 10 cm pots and measurements were taken 12 weeks after rooted cuttings were planted. Height measurements were taken from the soil line of the container. The plants were grown at 65°-68° F. night temperatures, under 3500-4000 foot candles of light, and 240 ppm nitrogen, 240 ppm potassium, and 175 ppm phosphorous nutritional levels with trace elements added. 5000 ppm B-9 was applied week three and week five of short day treatment of the six week short day treatment (14 hours dark) period. Habit of growth, plant height, flowering time, size of leaves and peduncle length will be greatly influenced by nutritional and environmental conditions.

Colors references are made to The Royal Horticultural Society Colour Chart except where general terms of ordinary dictionary significance are used.

Parentage: A controlled cross between female parent Tropicana and male parent Mikkelsen Seedling No. 84-2636-3.

Propagation:

(A) *Type cutting.*—Stem tip cutting up to 3 cm long.

(B) *Time to root.*—10 days at 21° C. in summer; 14 days at 21° C. in winter.

(C) *Rooting habit.*—Fibrous roots, fine, abundant.

Plant Description:

(A) *Habit and form of growth.*—Compact; semi-mounded to upright flower clusters above foliage; excellent branching; environment and use of growth regulators will play a role in final height.

(B) *Foliage description.*—Leaves simple and opposite. 1. Size: Average; full grown leaves on a plant grown in a 10 cm pot are 10 to 11 cm long and 9 to 9.5 cm wide. 2. Shape: Ovate, apex obtuse; base rounded. 3. Textrue: Glabrous, coriaceous, and succulent. 4. Margin: Crenate; moderately lobed. 5. Color: Young foliage, top side 146A; under side 138B. Mature foliage, top side 147A; underside 147B.

Flowering Description:

(A) *Flowering habits.*—Inflorescence is a cyme. Terminal flower on main axis opens first, followed by the terminal flowers of the side branches, continuing with the subsequent development of branches in the inflorescence. Inflorescence is made up of the main stem and up to eight or more lateral branches.

(B) *Natural flowering season.*—Early January. Flowering time under controlled daylength at 20° C. in summer is 10½ weeks; in winter 12 weeks. Flowering time depends on temperature, light intensity and other growing conditions.

(C) *Flower buds.*—Oblong, up to 4 mm long before showing color, developing tubular as flower petals mature; sheathed in four light green sepals.

(D) *Flowers borne.*—On compound dichasial cymes, primary penducle 5 mm in diameter just below the first branch of the inflorescence; length will vary depending on growing conditions. Pedicals vary in length depending on where they are located in the inflorescence.

(E) *Quantity of flowers.*—Very floriferous as the main stem plus eight or more laterals will have 40 or more flowers each.

(F) *Petals.*—1. Shape: Almost rounded; top cuspidate. 2. Color: Top side when opening 34A, fading to 34B; under side 34C. 3. Number of petals: Four. 4. Size: Individual petals 6 mm wide and 7 mm long; flowers 16 mm in diameter.

Reproductive organs:

1. Stamens.—Eight in number. a. Anther shape: Flat, elliptical, color yellow-green. b. Filament color: Yellow-green. c. Pollen color: Yellow.
2. *Pistils.*—a. Stigma shape: Flat, mature color whitish. b. Style color: Light green. c. Ovaries: four; size 4 mm; color green.

Disease Resistance: Splendor has shown resistance to Powdery Mildew and no diseases have been noted to date.

Other Important Characteristics: Splendor is part of a series of Kalanchoe plants that include Revelry, Majestic, Keepsake and Heirloom (all disclosed in pending plant patent applications of applicant) that are similar in flowering time, height, branching and response to growth regulators. This allows the greenhouse grower to handle all five distinctly different colors at the same time from a single planting date and use the same growing methods on each to end up with a uniform crop. The end results are easier crops for the grower to produce and higher quality crops. All cultivars are idel for 10 and 15 cm pot production.

I claim:

1. A new and distinct cultivar of Kalanchoe plant named Splendor, as illustrated and described.

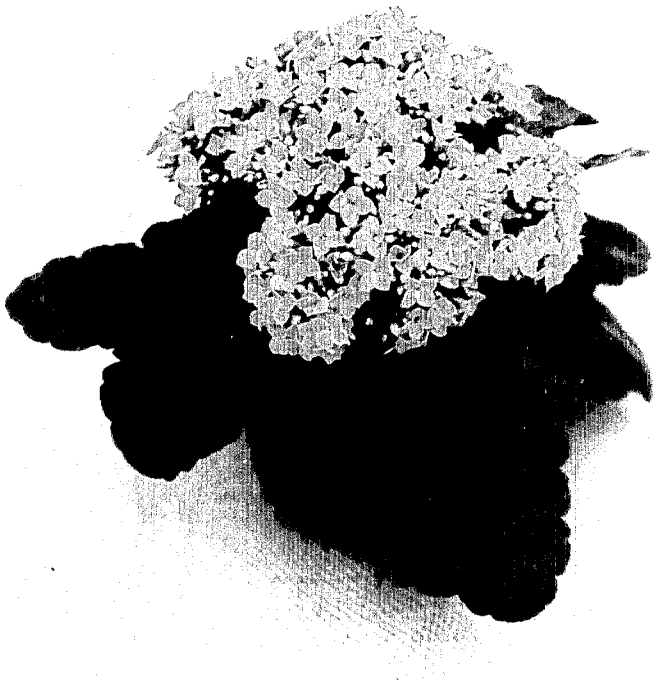

* * * * *